(12) United States Patent
Schultheiss et al.

(10) Patent No.: US 7,537,572 B2
(45) Date of Patent: *May 26, 2009

(54) TREATMENT OR PRE-TREATMENT FOR RADIATION/CHEMICAL EXPOSURE

(75) Inventors: Reiner Schultheiss, Illighausen (CH); Wolfgang Schaden, Vienna (AT); John Warlick, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 547 days.

This patent is subject to a terminal disclaimer.

(21) Appl. No.: 11/238,524

(22) Filed: Sep. 29, 2005

(65) Prior Publication Data

US 2007/0239072 A1 Oct. 11, 2007

Related U.S. Application Data

(63) Continuation-in-part of application No. 11/122,154, filed on May 4, 2005, now Pat. No. 7,470,240, and a continuation-in-part of application No. 11/071,156, filed on Mar. 4, 2005.

(60) Provisional application No. 60/690,851, filed on Jun. 15, 2005, provisional application No. 60/621,028, filed on Oct. 22, 2004, provisional application No. 60/642,149, filed on Jan. 10, 2005.

(51) Int. Cl.
*A61H 1/02* (2006.01)

(52) U.S. Cl. .............................. 601/2; 601/4; 600/437; 600/427

(58) Field of Classification Search .................. 601/2–4; 600/437–461, 427
See application file for complete search history.

(56) References Cited

U.S. PATENT DOCUMENTS

| 3,951,140 A | 4/1976 | Eggleton et al. |
|---|---|---|
| 4,539,989 A | 9/1985 | Forssmann et al. |
| 4,807,627 A | 2/1989 | Eisenmenger |
| 4,905,671 A | 3/1990 | Senge et al. |

(Continued)

FOREIGN PATENT DOCUMENTS

DE 197 21 218 A1 11/1998

(Continued)

OTHER PUBLICATIONS

R.Meirer, et al; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier Ltd.

(Continued)

*Primary Examiner*—Brian Casler
*Assistant Examiner*—John F Ramirez
(74) *Attorney, Agent, or Firm*—David L King

(57) ABSTRACT

A method of treatment for a tissue organ or entire body of a patient prior to or after exposure to chemicals or radiation or both comprises the steps of activating an acoustic shock wave generator or source to emit acoustic shock waves; and subjecting the tissue, organ or entire body to the acoustic shock waves stimulating said tissue, organ or body wherein the tissue, organ or body is positioned within a path of the emitted shock waves.

14 Claims, 8 Drawing Sheets

U.S. PATENT DOCUMENTS

| | | | |
|---|---|---|---|
| 4,984,575 A * | 1/1991 | Uchiyama et al. | 600/439 |
| 5,119,801 A | 6/1992 | Eizenhoefer et al. | |
| 5,174,280 A | 12/1992 | Gruenwald et al. | |
| 5,222,484 A | 6/1993 | Krauss et al. | |
| 5,419,335 A | 5/1995 | Hartmann | |
| 5,545,124 A | 8/1996 | Krause et al. | |
| 5,583,159 A | 12/1996 | Horrobin et al. | |
| 5,595,178 A | 1/1997 | Voss et al. | |
| 5,716,608 A | 2/1998 | Byram et al. | |
| 6,036,661 A * | 3/2000 | Schwarze et al. | 601/4 |
| 6,068,596 A | 5/2000 | Weth et al. | |
| 6,186,963 B1 | 2/2001 | Schwarze et al. | |
| 6,217,531 B1 | 4/2001 | Reitmajer | |
| 6,368,292 B1 | 4/2002 | Ogden et al. | |
| 6,390,995 B1 | 5/2002 | Ogden et al. | |
| 2002/0002345 A1 | 1/2002 | Marlinghaus | |
| 2003/0129154 A1 | 7/2003 | McDaniel | |
| 2004/0059265 A1 * | 3/2004 | Candy et al. | 601/2 |
| 2004/0162508 A1 | 8/2004 | Uebelacker | |
| 2005/0010140 A1 | 1/2005 | Forssmann | |
| 2005/0038362 A1 | 2/2005 | Schultheiss | |
| 2005/0075587 A1 | 4/2005 | Vago | |
| 2006/0051328 A1 | 3/2006 | Johnson | |

FOREIGN PATENT DOCUMENTS

| | | |
|---|---|---|
| DE | 103 11 659 | 9/2004 |
| EP | 0 243 947 A1 | 4/1987 |
| EP | 0 324 711 A2 | 1/1989 |
| EP | 1 146 885 B1 | 1/2000 |
| EP | 1 445 758 | 8/2004 |
| WO | WO 02/069892 A2 | 9/2002 |
| WO | WO 2005/007118 A2 | 1/2005 |
| WO | WO 2005/018600 A2 | 3/2005 |
| WO | WO 2005/063334 A1 | 7/2005 |
| WO | WO 2005/075020 | 8/2005 |

OTHER PUBLICATIONS

T. Nishida, et al; Extracorporeal Cardiac Shock Wave Therapy Markedly Ameliorates Ischemia-Induced Myocardial Dysfunction in Pigs in Vivo; Circulation; Nov. 9, 2004; Circulation. 2004; 110; pp. 3055-3061.

L.Gerdesmeyer, et al; Antibacterial Effects of Extracorporeal Shock Waves;World Fed for Ultrasound in Medicine & Biology;printed USA;Elsevier, vol. 31, No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990 Copyright 1990 by Academic Press, Inc.

Jagadeesh, G. et al;"Novel applications of micro-shock waves in biological sciences", J. Indian Inst. Sci. 2002, 82, pp. 1-10.

Thiel, M. et al; "The use of shock waves in medicine-a tool of the modern OR; an overview of basic physical principles, history and research", Min Invas Ther & Allied Technol 2000; 9(3/4) 247-253.

Huemer, Georg M. et al; "Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

* cited by examiner

TREATMENT OR PRE-TREATMENT FOR RADIATION/CHEMICAL EXPOSURE

RELATED APPLICATIONS

This application is a continuation in part of U.S. patent application Ser. No. 11/122,154 filed on May 4, 2005 now U.S. Pat. No. 7,470,240 entitled "Pressure Pulse/Shock Wave Therapy Methods and an Apparatus for Conducting the Therapeutic Methods" and U.S. patent application Ser. No. 11/071,156 filed on Mar. 4, 2005 entitled "Pressure Pulse/Shock Wave Apparatus for Generating Waves Having Nearly Plane or Divergent Characteristics" and also claims benefit of priority to U.S. Provisional Patent Application Ser. No. 60/690,851 filed Jun. 15, 2005, U.S. Provisional Patent Application Ser. No. 60/621,028 filed Oct. 22, 2004 and of U.S. Provisional Patent Application Ser. No. 60/642,149 filed Jan. 10, 2005, the disclosures of which are incorporated herein by reference in their entirety.

FIELD OF THE INVENTION

This invention relates to treatments for protecting or healing tissue and organs from the effects of exposure to radiation and or chemicals.

BACKGROUND OF THE INVENTION

Exposure to radiation or invasive chemical agents causes serious cellular damage which has been virtually irreversible. Once exposed the tissue's ability to fight damaging effects of such exposures is greatly diminished if not eliminated.

Scientists have developed some promising and novel concepts to pre-condition mammals to be more resistant to such exposures. In EP 1 146 885 B1 Canadian Scientists from the University of Montreal developed a pre-conditioning treatment for mammalian patients to better withstand external cellular insults likely to effect acceleration of or to increase the degree of apoptosis or necrosis in the tissues or organs of the patient. More specifically against the harmful effects of chemical and radiation poisoning. Their objective was to provide a medicament for alleviating or decelerating the progression of symptoms of apoptosis or necrosis—related medical disorders. This patented technique is best described by a recitation of claim 1 which reads:

1. Use of an aliquot of blood from the mammalian body which has been extracted there from and reacted exvivo with at least one stressor selected from the group consisting of a temperature above or below body temperature, ultraviolet light and an oxidative environment for the manufacture of a medicament for use in alleviating or protecting against the symptoms of a disorder involving accelerated rates of apoptosis or necrosis in a mammalian body, said disorder, chemical exposure and ingestion disorder, neurodegenerative disorder, and physical trauma disorders, through reducing the rate of susceptibility to apoptosis or necrosis of tissues and organs of the mammalian body.

This procedure has noted benefits for pre-conditioning prior to exposure, but also notes benefits post-exposure.

In medicine a paradox occurs when one attempts to treat disorders with chemical or radiation. On the one hand dosages must be large enough to kill the infected site or tumorous growths while on the other hand limiting the migration or spill over which damages healthy non-affected tissues and organs.

Several prior art patents discuss at length the complications of such medical treatments. WO 021 069892 A2, an International publication by scientists at Temple University, discusses not only these therapeutic complications for a patient, but also radiation exposures to health care workers, dental practitioners, nuclear power plant workers and military personnel handling weapons or on nuclear powered vessels. Additionally this document discusses the well noted nuclear accidents such as Chernobyl, Tokamura and Three Mile Island as unintended exposures caused by power plant failures.

In WO 02/069892A2 it was stated "Pharmaceutical radiation sensitizers, which are known to preferentially enhance the effects of radiation in cancerous tissues, are clearly unsuited for general systemic protection of normal tissues from exposure to ionizing radiation." These scientists from Temple University found that $\alpha,\beta$-unsaturated aryl sulfones, in particular benzyl styryl sulfones, provide significant and selective systemic protection of normal cells from radiation-induced damage in animals. When used in radiotherapy techniques, these compounds also showed independent toxicity to cancer cells. A remarkably and potentially complimentary finding to those of the present invention as will be discussed in the detailed description of the present invention.

More sinister types of exposures where lethality is the primary objective are thermal nuclear wars and terrorist acts involving lower yield so called dirty bomb radiation dispersions. In these cases the objective was to kill or maim on a large scale.

U.S. Pat. No. 5,583,159 teaches the use of medicaments to prevent internal radiation damage by ingesting medicaments containing GLA and or DGLA is disclosed.

WO 2005/007118 A2 published on Jan. 27, 2005 by Regenerx Biopharmaceuticals, Inc. of Bethesda Md. teaches a method of treatment or prevention of damage due to radiation exposure comprising administering to a subject in need of such treatment an effective amount of a composition comprising 1) a compound including a radiation damage-inhibiting polypeptide comprising amino acid sequence LKKTET, a conservative variant of LKKTET, an actin-sequestering agent, an anti-inflammatory agent; 2) an agent which stimulates production of said compound in said subject; 3) an agent which regulates said compound in said subject; or 4) an antagonist of said compound, so as to inhibit radiation damage in said subject.

In accordance with one embodiment, this prior art invention includes the treatment, prevention or reversal of physical, cognitive, and biological injuries resulting from exposure to ionizing radiation by the use of the peptide, Thymosin beta 4 (Thymosin $\beta4$ or T$\beta4$), or fragments of T$\beta4$ such as LKKTET, or conservative variants thereof. Sometimes these are referred to as LKKTET peptides or polypeptides. Included are N-or C-terminal variants such as KLKKTET and LKKTETQ.

T$\beta4$ stimulates the production of laminin-5 in cells which may protect, or facilitate repair of, tissue. T$\beta4$ was initially identified as a protein that is up-regulated during endothelial cell migration and differentiation in vitro. T$\beta4$ was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration and vascularization.

T$\beta4$ has been localized to a number of tissue and cell types and thus, agents which stimulate the production of T$\beta4$ can be added to or comprise a composition to effect T$\beta4$ production from a tissue and/or a cell. Such agents include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin al (Tal) and vascular endothelial growth factor (VEGF). More preferably, the agent is transforming growth factor beta (TGF-β) or other members of the TGF-β superfamily. Tβ4 compositions of the invention may reduce certain effects of radiation by effectuating growth of the connective tissue through extracellular matrix deposition, cellular migration and vascularization.

Additionally, other agents may be added to a composition along with Tβ4 or a Tβ4 isoform. Such agents include angiogenic agents, growth factors, agents that direct differentiation of cells, agents that promote migration of cells and agents that stimulate the provision of extracellular matrix material in tissue. For example, and not by way of limitation, Tβ4 or a Tβ4 isoform alone or in combination can be added in combination with any one or more of the following agents: VEGF, KGF, FGF, PDGF, TGFβ, IGF-1, IGF-2, IL-1, prothymosin a and thymosin al in an effective amount.

The actual dosage or reagent, formulation or composition that heals damage associated with radiation damage may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

According to these prior art inventors, suitable formulations include the inventive composition at a concentration within the range of about 0.001-10% by weight, more preferably within the range of about 0.005-0.1% by weight, most preferably about 0.01-0.05% by weight.

The therapeutic approaches described therein involved various routes of administration or delivery of reagents or compositions comprising the Tβ4 or other compounds of this prior art invention, including any conventional administration techniques (for example, but not limited to, topical administration, local injection, inhalation, systemic or enteral administration), to a subject. The methods and compositions using or containing Tβ4 or other compounds of the invention may be formulated into pharmaceutical compositions by admixture with pharmaceutically acceptable non-toxic excipients or carriers.

All of these above referenced prior art treatments for damage prevention from exposure to radiation involve some form of medicament or radiation blocking medication.

An objective of the present invention is to compliment these radiation exposure pharmaceutical treatments by increasing the body's receptiveness to such treatments or to enable simplification of such drug compositions such that a drug induced activation of a healing cellular response mechanism is unnecessary altogether and thus such use of medicaments can be directed to treating the radiation or chemical agent induced effects of spreading infection and absorption of dead cells while the present invention complimentarily repairs and activates cellular repair and healthy cell regeneration to the exposed tissue and organs.

SUMMARY OF THE INVENTION

A method of treatment for a tissue, organ or entire body of a patient prior to or after exposure to chemicals or radiation or both comprises the steps of activating an acoustic shock wave generator or source to emit acoustic shock waves; and subjecting the tissue, organ or entire body to the acoustic shock waves stimulating said tissue, organ or body wherein the tissue, organ or body is positioned within a path of the emitted shock waves.

Definitions

"apoptosis" is the biological process of controlled, programmed cell death, by means of which cells die by a process of condensation without the release of cell contents into the surrounding milieu.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"cytoplasm" The part of a cell that contains the CYTOSOL and small structures excluding the CELL NUCLEUS; MITOCHONDRIA; and large VACUOLES.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"extracorporeal" occurring or based outside the living body.

A "generalized paraboloid" according to the present invention is also a three-dimensional bowl. In two dimensions (in Cartesian coordinates, x and y) the formula y″=2px [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"lactate dehydrogenase (LDH)" A tetrameric enzyme that, along with the coenzyme NAD+, catalyzes the interconversion of lactate and pyruvate. In vertebrates, genes for three different subunits (LDH-A, LDH-B and LDH-C) exist.

"mitochondria" Semiautonomous, self-reproducing organelles that occur in the cytoplasm of all cells of most, but not all, eukaryotes. Each mitochondrion is surrounded by a double limiting membrane. The inner membrane is highly invaginated, and its projections are called cristae. Mitochondria are the sites of the reactions of oxidative phosphorylation, which result in the formation of ATP. They contain distinctive RIBOSOMES, transfer RNAs (RNA, TRANSFER); AMINO ACYL T RNA SYNTHETASES; and elongation and termination factors. Mitochondria depend upon genes within the nucleus of the cells in which they reside for many essential messenger RNAs (RNA, MESSENGER). Mitochondria are believed to have arisen from aerobic bacteria that established a symbiotic relationship with primitive protoeukaryotes.

"necrosis" A pathological process caused by the progressive degradative action of enzymes that is generally associated with severe cellular trauma. It is characterized by mitochondrial swelling, nuclear flocculation, uncontrolled cell lysis, and ultimately CELL DEATH.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"phagocytosis" The engulfing of microorganisms, other cells, and foreign particles by phagocytic cells.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100's of ns. The duration of a shock wave is typically below 1-3 micro-seconds (μs) for the positive part of a cycle and typically above some micro-seconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1A:
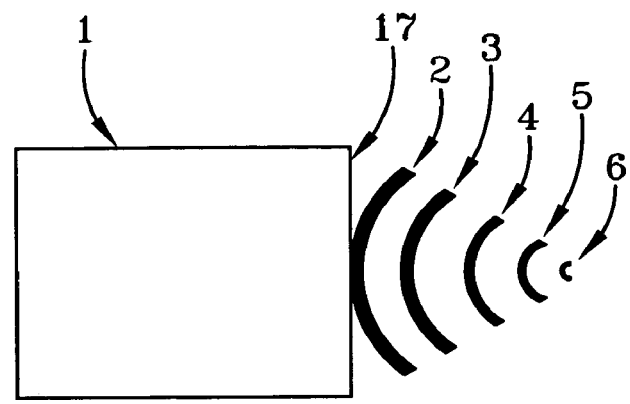
FIG. 1a is a simplified depiction of a pressure pulse/shock wave (PP/SW) generator with focusing wave characteristics.

In the shock wave method of treating a tissue, an organ or the entire body of a mammal be it human or an animal with a risk of exposure to chemical or radiation or post-occurrence of such an exposure requires the patient to be positioned in a convenient orientation to permit the source of the emitted waves to most directly send the waves to the target site to initiate shock wave stimulation of the target area with minimal, preferably no obstructing features in the path of the emitting source or lens. Assuming the target area is within a projected area of the wave transmission, a single transmission dosage of wave energy may be used. The transmission dosage can be from a few seconds to 20 minutes or more dependant on the condition. Preferably the waves are generated from an unfocused or focused source. The unfocused waves can be divergent, planar or near planar and having a low pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the tissue or organ does not have to experience the sensation of hemorrhaging so common in the higher energy focused wave forms having a focal point at or within the targeted treatment site.

If the target site is an organ subjected to a surgical procedure exposing at least some if not all of the organ within the body cavity the target site may be such that the patient or the generating source must be reoriented relative to the site and a second, third or more treatment dosage can be administered. The fact that the dosage can be at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments.

The present method does not rely on precise site location per se, although can be used in combination with such known devices as ultrasound, cat-scan or x-ray imaging if needed. The physician's general understanding of the anatomy of the patient should be sufficient to locate the target area to be treated. This is particularly true when the exposed tissue or portion of the irradiated body or organ is visually within the surgeon's line of sight and this permits the lens or cover of the emitting shock wave source to impinge on the organ or tissue directly or through a transmission enhancing gel, water or fluid medium during the shock wave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating stem cell activation or a cellular release or activation of VEGF and other growth factors.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm. A key advantage of the present inventive methodology is that it is complimentary to conventional medical procedures. In the case of any operative surgical procedure the surgical area of the patient can be bombarded with these low energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced but also the number of applied shock wave impulses can be lowered from several thousand to as few as one or more pulses and still yield a beneficial stimulating response.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted organ or tissue to generate new growth or to regenerate weakened vascular networks in for example the cardio vascular system. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patients own body activating the naturally occurring stem cells or stem cells that have been introduced to the patient as part of a treatment beneficially utilizing stem cells. This is a significant clinical value in its own right.

In one embodiment, the invention provides for germicidal cleaning of diseased or infected areas and for wound cleaning generally after exposure to chemical agents or radiation.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factors thereby inducing or accelerating healing.

The unfocused shock waves can be of a divergent wave pattern, planar or near planar pattern preferably of a low peak pressure amplitude and density. Typically the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 $cm^2$ commonly produced by focused waves. The above methodology is particularly well suited for surface as well as sub-surface soft tissue organ treatments.

The above methodology is valuable in generation of tissue, vascularization and may be used in combination with stem cell therapies as well as regeneration of tissue and vascularization.

The methodology is useful in (re)vascularization and regeneration of the heart, brain, liver, kidney and skin.

The methodology is useful in stimulating enforcement of defense mechanisms in tissue cells to fight infections from bacteria and can be used germicidally to treat or cleanse wounds or other target sites which is a primary concern in the case of chemical or radiation burns resulting from such exposures to radiation or chemical agents.

While the above listed indications cited above are not exhaustive nor intended to be limiting, it is exemplary of the wide range of beneficial uses of low energy and amplitude unfocused divergent, planar or nearly planar shock waves, convergent shock waves, diffused shock waves or a combination of shock wave types in the treatment of humans and other mammals that are exposed to chemical or radiation or are about to be so exposed as the result of a therapeutic treatment or are at potential risk to such exposure.

A most significant method of preventive medicine can be practiced that is fully enabled by the use of these relatively low amplitude and pressure shock waves. The method includes the steps of identifying high risk patients for a variety of potential chemical or radiation risk conditions. Such condition could be by way of example cancer treatments. After identifying a risk prone candidate providing one or a series of two or more exposure treatments with unfocused, divergent, planar or near planar shock waves or convergent far-sighted focused shock waves or diffused shock waves to the treatment site, in this example the region surrounding or in proximity to malignant cells or tumors. Then after treatments the physician can optionally ultrasound visually or otherwise determine the increase in regeneration or vascularization in the treated tissue after a period of time. Assuming an initial baseline determination of the tissue regeneration or vascularization had been initially conducted an estimate or calculation of dosage requirements can be made. This procedure can be used for any at risk condition. After such a chemical or radiological treatment the surrounding tissues can be post-operatively shock wave treated as well.

The implications of using the (re)generative features of this type of shock wave therapy are any weakened organ or tissue even teeth or bone can be strengthened to the point of reducing or eliminating the risk of irreparable damage or failure.

The stimulation of growth factors and activation of healing acceleration within the cells of the treated tissues is particularly valuable to cancer patients and other high risk factor subjects exposed to radiation or chemical agents.

Even more striking as mentioned earlier, early prevention therapies can be employed to stimulate tissue or organ modeling to be maintained within acceptable ranges prior to an exposure to damaging chemicals or radiation occurring. This is extremely valuable in the prevention of radiation poisoning for example. The methods would be to identify at risk patients or workers based on family history and exposure risks, and subjecting that patient or worker to therapeutic shock wave therapy for the purpose of stimulating tissue repair or regeneration effectively remodeling the patient's susceptible organs to be within accepted functional parameters prior to exposure. The objective being to preventively stimulate cellular tissue repairs to preemptively avoid a degenerative condition from occurring which may result in the onset of cancer and require invasive surgical procedures.

This preventive therapy is most needed to combat damaging chemical or radiation exposure which left untreated results in cellular destruction or any other degenerative conditions.

FIG. 1a is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

Figure 1B:
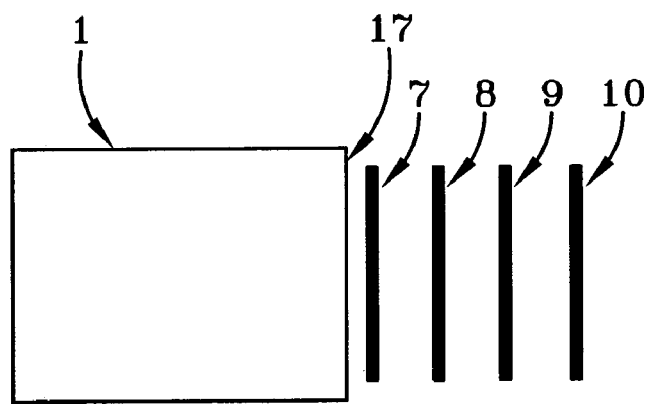
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
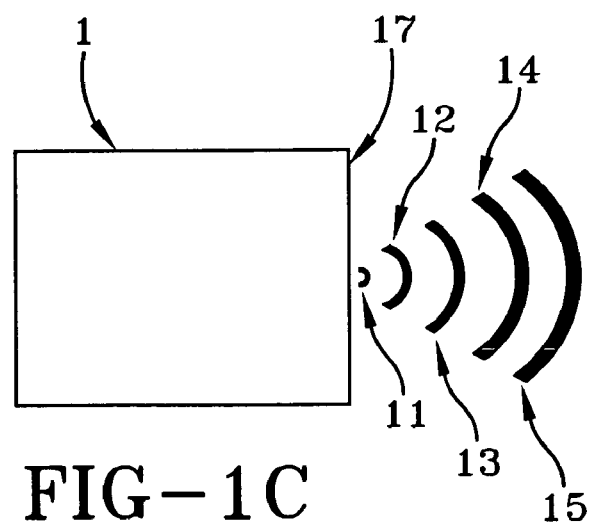
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2b.

Figure 2A:
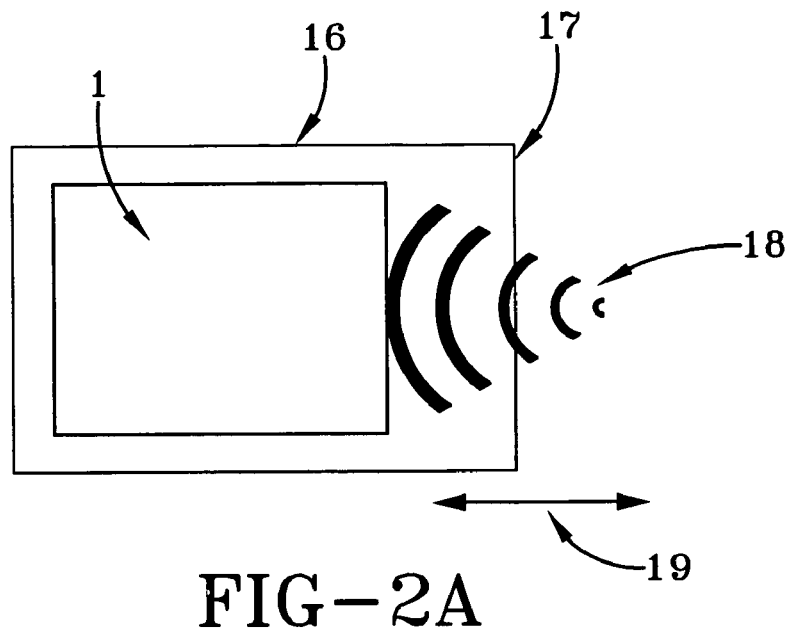
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
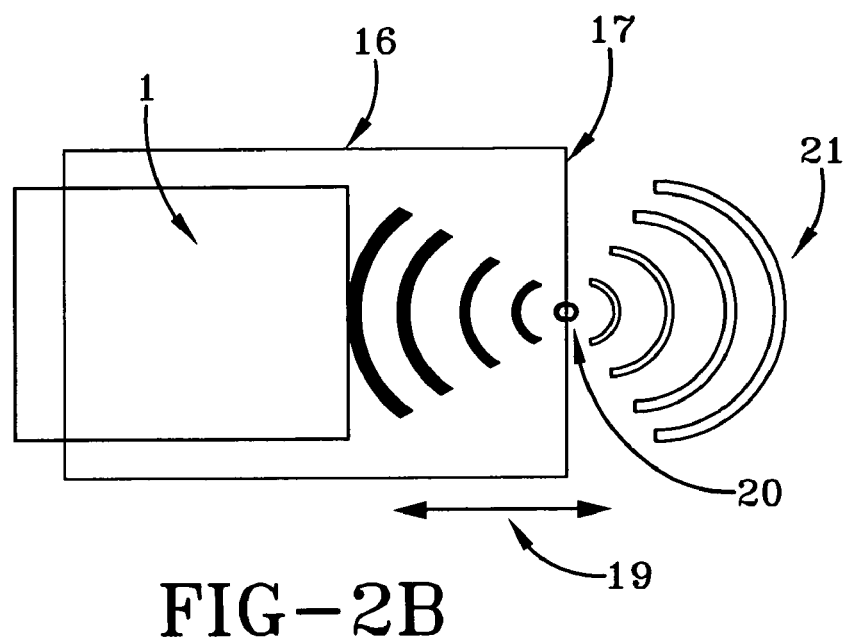
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
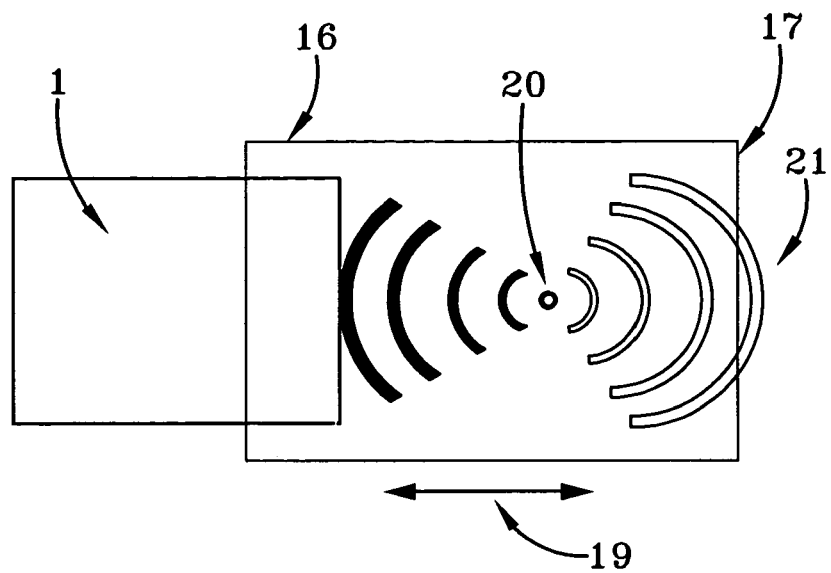
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
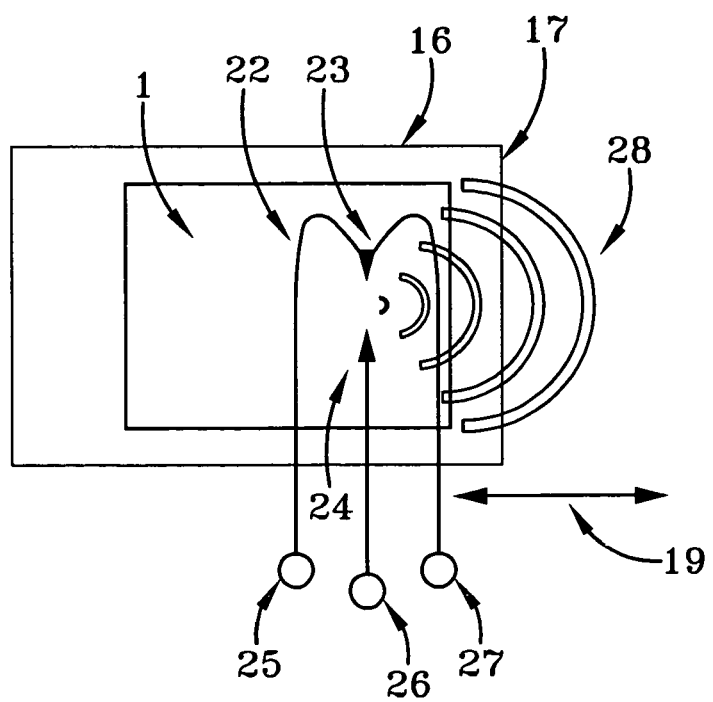
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
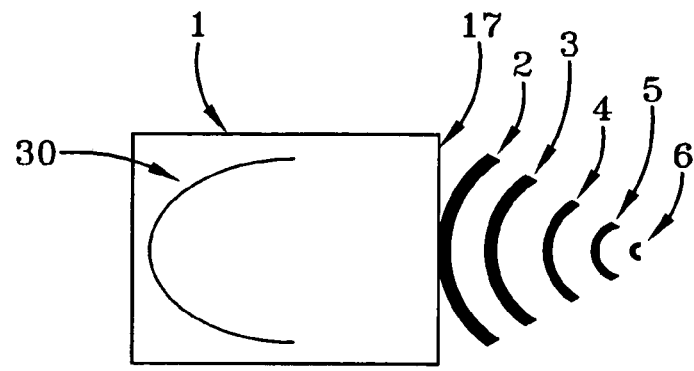
FIG. 4a is a simplified depiction of a pressure pulse/shock wave generator having a focusing element in the form of an ellipsoid. The waves generated are focused.

FIG. 4a is a simplified depiction of the pressure pulse/ shock wave generator (shock wave head) having as focusing element an ellipsoid (30). Thus, the generated waves are focused at (6).

Figure 4B:
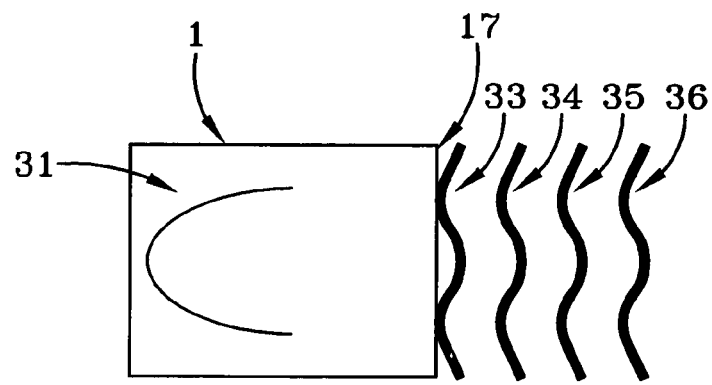
FIG. 4b is a simplified depiction of a pressure pulse/shock wave generator having a parabolic reflector element and generating waves that are disturbed plane.

FIG. 4b is a simplified depiction of the pressure pulse/ shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
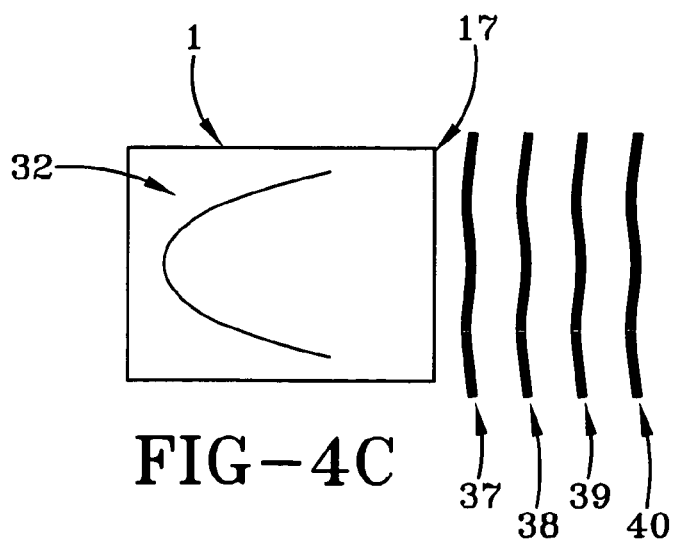
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/ shock wave generator (shock wave head) having as a focusing element a generalized paraboloid ($y^n=2px$, with $1.2<n<2.8$ and $n\neq2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
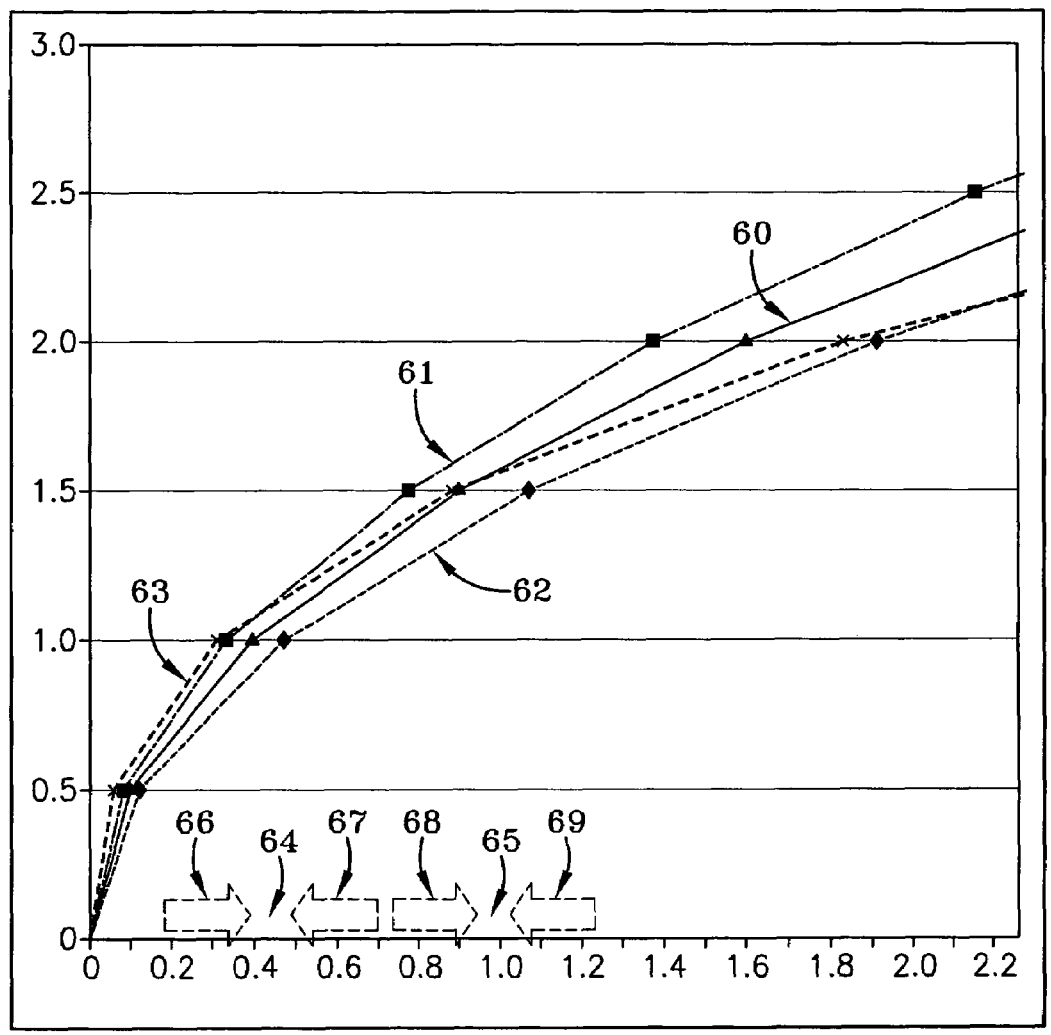
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n\neq2$ and a p value of about 1.55 cm. The generalized paraboloid compensates for different p values that result from the electrode burn down and/or adjustment of the electrode tips.

Figure 5:
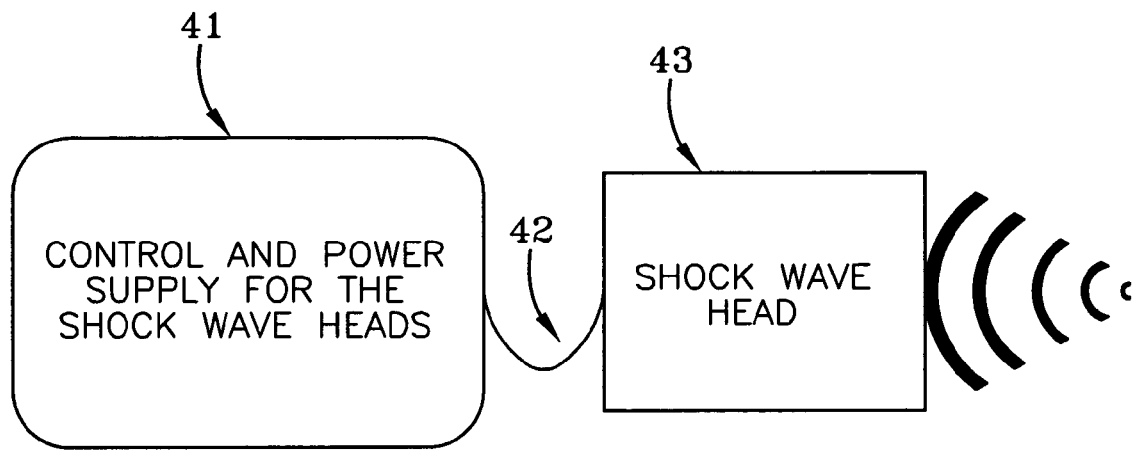
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
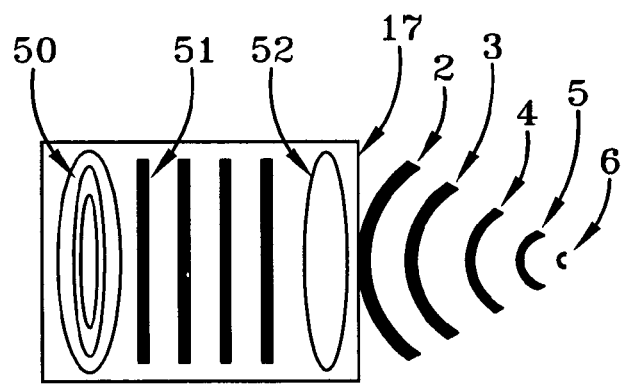
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
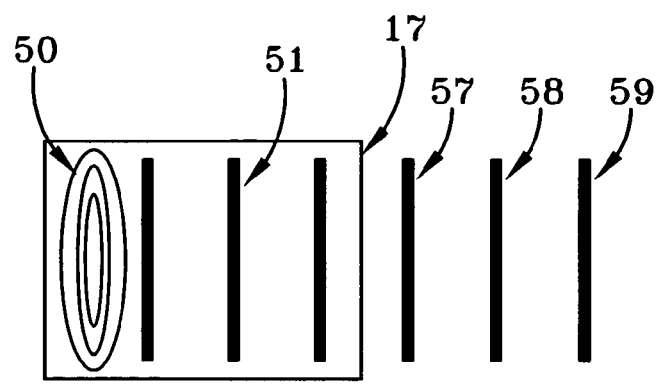
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
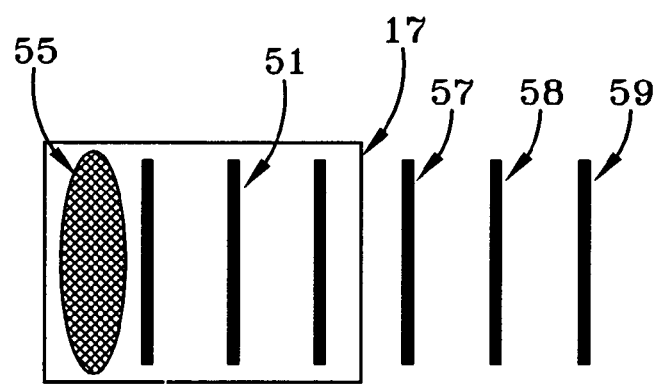
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
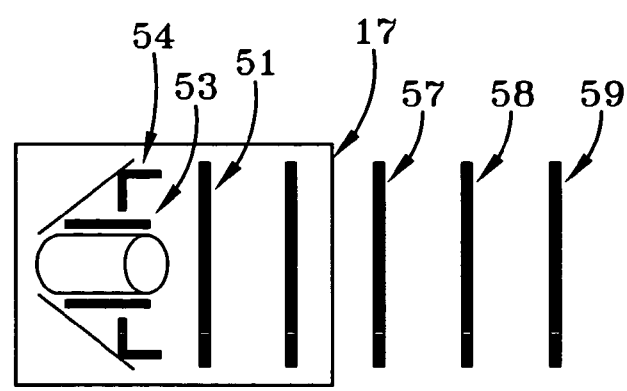
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
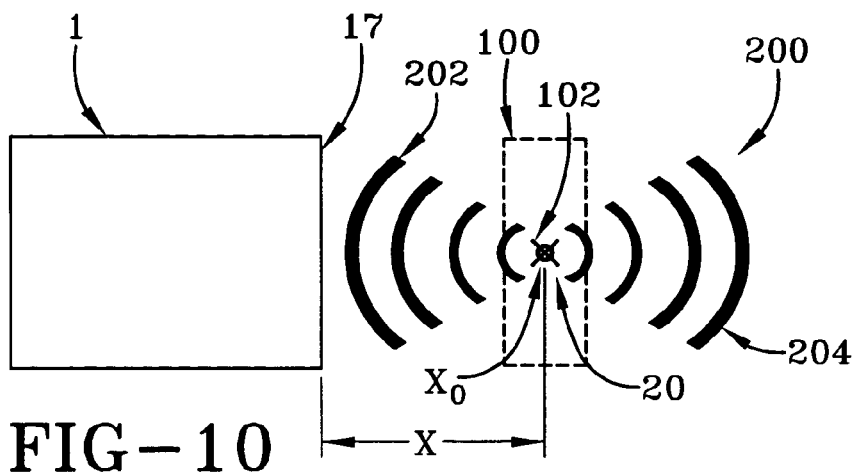
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
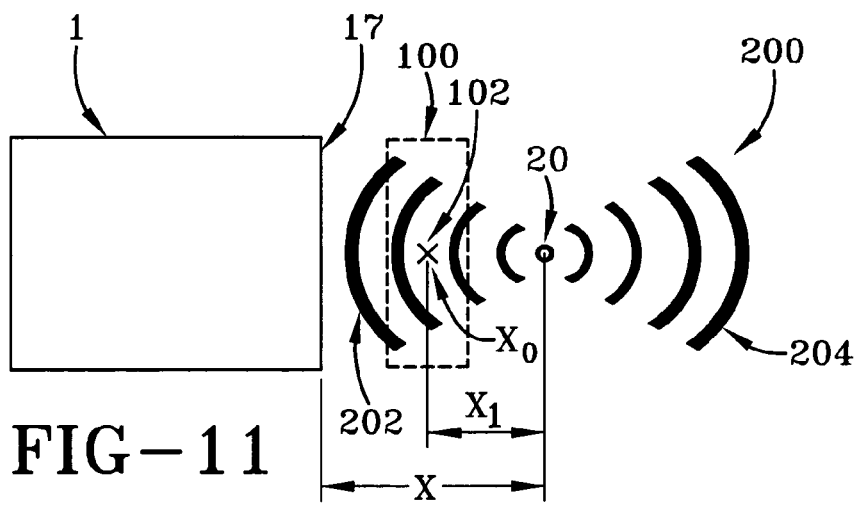
FIG. 11 is a simplified depiction of a pressure pulse/shock wave (PP/SW) generator with the focusing wave characteristics shown wherein the focus is located a distance $X_1$ from the location $X_0$ of an organ wherein the converging waves impinge the organ.
Figure 12:
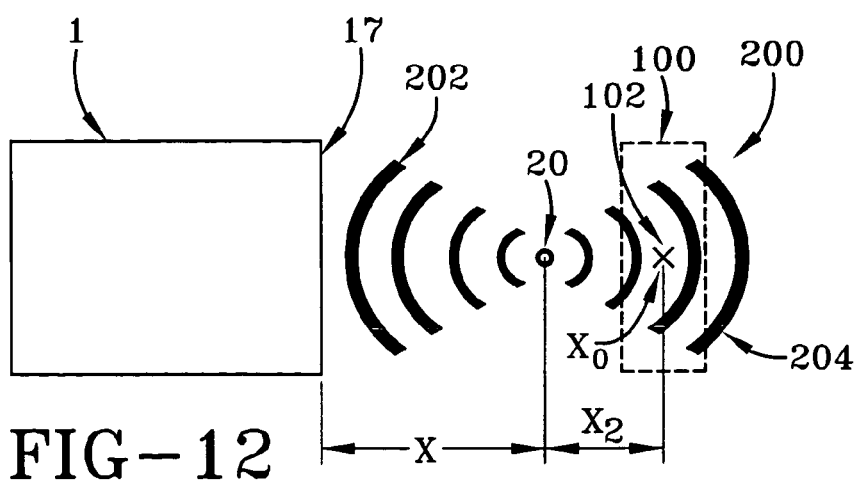
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 an organ 100 is shown generally centered on the focal point or volume 20 at a location $X_0$ within the organ 100. In this orientation the emitted waves are focused and thus are emitting a high intensity acoustic energy at the location $X_0$. This location $X_0$ can be anywhere within or on the organ. Assuming the organ 100 is a tissue having a mass 102 at location $X_0$ then the focus is located directly on the mass 102. In one method of treating a tumor or any other type mass 102 these focused waves can be directed to destroy or otherwise reduce the mass 102.

With reference to FIG. 11, the organ 100 is shifted a distance X toward the generator or source 1. The organ 100 at location $X_0$ being positioned a distance $X-X_1$ from the source 1. This insures the organ 100 is impinged by converging waves 202 but removed from the focal point 20. When the organ 100 is tissue this bombardment of converging waves 202 stimulates the cells activating the desired healing response as previously discussed.

With reference to FIG. 12, the organ 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the organ 100 which when the organ is a cellular tissue stimulates the cells to produce the desired healing effect or response.

Heretofore such invasive techniques were not used in combination with shock wave therapy primarily because the shock waves were believed to be able to sufficiently pass through interfering body tissue to achieve the desired result in a non-invasive fashion. While this may be true, in many cases if the degenerative process is such that an operation is required then the combination of an operation in conjunction with shock wave therapy only enhances the therapeutic values and the healing process of the patient and the organ such that regenerative conditions can be achieved that would include not only revascularization of the heart or other organs wherein sufficient or insufficient blood flow is occurring but also to enhance the improvement of ischemic tissue that may be occupying a portion of the organ. This ischemic tissue can then be minimized by the regenerative process of using shock wave therapy in the fashion described above to permit the tissue to rebuild itself in the region that has been afflicted.

As shown in FIGS. 1-12 the use of these various acoustic shock wave forms can be used separately or in combination to achieve the desired therapeutic effect.

Furthermore such acoustic shock wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having nearly plane or even divergent characteristics. With an unfocused wave having nearly plane wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having nearly plane or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output.

The treatment of the above mentioned tissue, organ or body of a patient or worker believed to be a first time use of acoustic shock wave therapy in the preventive pre-exposure or post-exposure to chemical agents or radiation. None of the work done to date has treated the above mentioned exposures with convergent, divergent, planar or near-planar acoustic shock waves of low energy or focused shock waves in a path from the emitting source lens or cover. Also this is believed to be a first time use of acoustic shock waves for germicidal wound cleaning or preventive medical treatments for such exposures.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

The use of acoustic shock waves to patients exposed to chemical agents or drugs or to radiation exposure stimulates a cellular response of the treated tissues as well as a cellular response in the surrounding tissue. This response activates otherwise dormant cells to increase the body's own defense mechanisms, allowing the cells to limit the migration of tissue damage, but also to initiate the healing process. This feature means that the treating physician has the added benefit of a patient whose body will be strengthened to mitigate damage to otherwise healthy tissues and organs.

The nature of cancer treatments employing a combination of chemicals and radiation exposure to kill cancerous cells is well known to weaken the entire body's ability to defend from infections and associated diseases. The result is the patient is in a greatly weakened state overall. These treatments are so severe that the common problems of hair loss and overall nausea are well documented. These symptoms are generally reversible. The more serious complications are not reversible. In some cases gum damage and complete destruction of the teeth has been observed as a consequence of such treatments. The treatments are both cumulative in their adverse reactions and thus the effective treatment of the cancer cells also permanently damages otherwise healthy tissue and organs. The use of the shock waves as described above stimulates these healthy cells to defend against this spill over intrusion.

This means the physician can use these treatments with far less adverse reactions if he combines the treatments with one or more exposures to acoustic shock waves either before introducing chemical agents or radiation or shortly thereafter or both. This further means that the patient's recovery time should be greatly reduced because the patient treated with shock waves will have initiated a healing response that is much more aggressive than heretofore achieved without the cellular stimulation. The current use of medications to stimulate such cellular activity is limited to absorption through the bloodstream via the blood vessels. Acoustic shock waves stimulate all the cells in the region treated activating an almost immediate cellular release of healing agents. Furthermore, as the use of otherwise conflicting chemicals is avoided, adverse side effects can be limited to those medicaments used to destroy the cancerous cells. In other words the present invention is far more complimentary to such chemotherapy and radiation treatments in that the stimulation of otherwise healthy cells will greatly limit the adverse and irreversible effects on the surrounding non-cancerous tissues and organs.

A further benefit of the use of acoustic shock waves is there are no known adverse indications when combined with the use of other medications or drugs. In fact the activation of the cells exposed to shock wave treatments only enhances cellular absorption of such medication making these drugs faster acting than when compared to non stimulated cells. As a result, it is envisioned that the use of one or more medicaments prior to, during or after subjecting the patient to acoustic shock waves will be complimentary to the treatment or pre-conditioning treatment for radiation or chemical exposures. It is further appreciated that certain drug therapies can be altered or modified to lower risk or adverse side effects when combined with a treatment involving acoustic shock waves as described above.

In the case wherein the patient is a victim of a chemical agent or radiation exposure as the result of an accident or an attack, the immediate use of shock waves shortly after exposure can be an effective tool in saving lives. The body's ability to recover is enhanced and the damaged tissue can be more quickly replaced by stimulated healthy cells which is a regenerative feature of the use of shock wave treatments.

This is particularly true in the case of chemical or radiation burns of the skin caused by agents like mustard gas or radiation. The wounded tissue is a source of infection which can lead to a complete failure of the body leading to death. The use of shock wave treatments is a valuable tool in such a case because acoustic shock waves can be provided on a virtually limitless basis as long as connected to an adequate power source. Normally supplies of medicines are limited and almost never near the area most in need. Accordingly vehicles similar to emergency trucks used to transport patients can be equipped with shock wave generators so that in field treatments can be conducted on a wide scale quickly. This alone could greatly reduce the loss of life that would occur by delays in treatment.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. The method of treatment for a tissue, organ or entire body of a patient after exposure to chemicals, radiation or both comprises the steps of:
   treating a patient after exposure to chemicals, radiation or both;
   activating an acoustic shock wave or pressure pulse generator or source to emit pressure pulses or acoustic shock waves directed toward the tissue to impinge the tissue with shock waves having a low energy density in the range of 0.000001mJ/mm² to 1.0mJ/mm², the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (µs) for the positive part of a cycle and typically above some micro-seconds for the negative part of a cycle; and
   subjecting the tissue, organ or entire body to convergent, divergent, planar or near planar acoustic shock waves or pressure pulses treatment energy density and treatment dosage stimulating said tissue, organ or body wherein the tissue, organ or body is positioned within a path of the emitted shock waves and away from any localized geometric focal volume or point of the emitted shock waves wherein the emitted shock waves or pressure pulses either have no geometric focal volume or point or have a focal volume or point ahead of the tissue or beyond the tissue thereby passing the emitted waves or pulses through the tissue while avoiding having any localized focal point within the tissue and wherein the emitted pressure pulses or shock waves are convergent, divergent, planar or near planar and the pressure pulse shock wave generator or source is based on electrohydraulic, electromagnetic, piezoceramic or ballistic wave generation having an energy density value ranging as low as 0.00001 mJ/mm² to a high end of below 1.0 mJ/mm².

2. The method of treatment of claim 1 wherein the emitted shock waves or pressure pulses are convergent having one or more geometric focal volumes of points at a distance of at least X from the generator or source, the method further comprising positioning the organ at a distance at or less than the distance X from the source.

3. The method of treatment of claim 1 further comprises the step of: administering one or more medicaments prior, during or after subjecting the patient to acoustic shock waves or pressure pulses.

4. The method of treatment of claim 1 further comprises the step of: directing radiation to a predetermined treatment region to eradicate cancerous cells or tissue.

5. The method of treatment of claim 1 further comprises the step of: administering a treatment of chemotherapy to eradicate cancerous cells or tissue.

6. The method of treatment of claim 1 further comprises the step of: subjecting a tissue or organ to a surgical procedure to remove some or all of a cancerous growth or tumor.

7. The method of treatment of claim 1 wherein the exposure to chemicals or radiation is the result of an accident or act of aggression and the method further comprises the steps of: setting up a treatment site; selecting patients suffering from exposure; and treating said patients to the shock waves or pressure pulses.

8. The method of treatment of claim 7 further comprises the step of: providing mobile or vehicle contained acoustic shock wave or pressure pulse generators; and delivering said generators to said treatment sites.

9. The method of treatment for a tissue, organ or entire body of a patient prior to exposure to chemicals, radiation or both comprises the steps of:
   receiving the patient pre-occurrence to being exposed to chemicals, radiation or both;
   activating an acoustic shock wave or pressure pulse generator or source to emit acoustic shock waves or pressure pulses directed toward the tissue to impinge the tissue with shock waves or pressure pulses having a low energy density in the range of 0.000001 mJ/mm² to 1.0 mJ/mm², the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms),the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle; and subjecting the tissue, organ or entire body to convergent, divergent, planar or near planar acoustic shock waves or pressure pulses treatment energy density and treatment dosage stimulating said tissue, organ or body in the absence of creating cavitation bubbles in the treated tissue, organ or body wherein the treated tissue, organ or body is positioned within a path of the emitted shock waves or pressure pulses and away from any localized geometric focal volume or point of the emitted shock waves or pressure pulses wherein the emitted shock waves or pressure pulses either have no geometric focal volume or point or have a focal volume or point ahead of the tissue or beyond the tissue thereby passing the emitted waves or pulses through the tissue while avoiding having any localized focal point within the tissue wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$; both the treatment energy density and treatment dosage are selected to avoid cell damage as evidenced by the avoidance of cell hemorrhaging within the tissue caused by cavitation.

10. The method of treatment of claim 9 wherein the emitted shock waves or pressure pulses are convergent having one or more geometric focal volumes of points at a distance of at least X from the generator or source, the method further comprising positioning the organ at a distance at or less than the distance X from the source.

11. The method of treatment of claim 9 further comprises the step of: administering one or more medicaments prior, during or after subjecting the patient to acoustic shock waves.

12. The method of treatment of claim 9 further comprises the step of: directing radiation to a predetermined treatment region to eradicate cancerous cells or tissue.

13. The method of treatment of claim 9 farther comprises the step of: administering a treatment of chemotherapy to eradicate cancerous cells or tissue.

14. The method of treatment of claim 9 further comprises the step of: subjecting a tissue or organ to a surgical procedure to remove some or all of a cancerous growth or tumor.

* * * * *